(12) United States Patent
Hoshino et al.

(10) Patent No.: US 7,291,138 B2
(45) Date of Patent: Nov. 6, 2007

(54) DISPOSABLE ABSORBENT ARTICLE

(75) Inventors: Minoru Hoshino, Kiryu (JP); Fumiko Aoki, Gunma (JP); Terumasa Kondo, Gunma (JP)

(73) Assignee: Hakujuji Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/530,454

(22) PCT Filed: Dec. 12, 2003

(86) PCT No.: PCT/JP03/15970

§ 371 (c)(1),
(2), (4) Date: Apr. 5, 2005

(87) PCT Pub. No.: WO2004/054482

PCT Pub. Date: Jul. 1, 2004

(65) Prior Publication Data

US 2006/0036227 A1     Feb. 16, 2006

(30) Foreign Application Priority Data

Dec. 13, 2002   (JP)   ............................. 2002-362957

(51) Int. Cl.
*A61F 13/30*   (2006.01)
(52) U.S. Cl. ..................... 604/385.27; 604/385.24; 604/385.25; 604/385.29; 604/385.3; 604/396; 604/385.01; 604/358
(58) Field of Classification Search ........... 604/385.27, 604/385.24, 385.25, 385.29, 385.3, 396, 604/385.01, 358
See application file for complete search history.

(56) References Cited

U.S. PATENT DOCUMENTS

| | | | | |
|---|---|---|---|---|
| 3,766,922 A | * | 10/1973 | Krusko | ....................... 604/374 |
| 5,858,012 A | * | 1/1999 | Yamaki et al. | ......... 604/385.27 |
| 6,369,291 B1 | * | 4/2002 | Uchimoto et al. | .......... 604/367 |
| 6,554,815 B1 | * | 4/2003 | Umebayashi | .......... 604/385.27 |
| 6,620,146 B2 | * | 9/2003 | Gibbs | ...................... 604/385.3 |

FOREIGN PATENT DOCUMENTS

| | | |
|---|---|---|
| JP | 3024357 | 5/1996 |
| JP | 09-038134 | 2/1997 |
| JP | 09-271488 | 10/1997 |
| JP | 10-127687 | 5/1998 |
| JP | 10-277091 | 10/1998 |
| JP | 11-332913 | 12/1999 |
| JP | 2001-178770 | 7/2001 |
| JP | 2002-165820 | 6/2002 |

* cited by examiner

*Primary Examiner*—Tatyana Zalukaeva
*Assistant Examiner*—Ginger Chapman
(74) *Attorney, Agent, or Firm*—Cheryl F. Cohen, LLC

(57) ABSTRACT

A rear elastic area formed by a rear waist region with rear waist elastic members stretchable laterally across the rear waist region. A front elastic area formed by a front waist region with front waist elastic members stretchable laterally across the front waist region. The rear waist region and the front waist region are capable of stretching or contracting in unison. A greater number of rear waist elastic members than front waist elastic members are provided. The rear elastic area is broader than the front elastic area with respect to the longitudinal direction of the diaper body. The body-hugging capability of the diaper body at the rear waist side of the wearer is increased so that the diaper body is prevented from slipping down. This configuration reduces constructive feeling by ensuring that the diaper body is not excessively tight at the front waist side of the wearer.

6 Claims, 4 Drawing Sheets

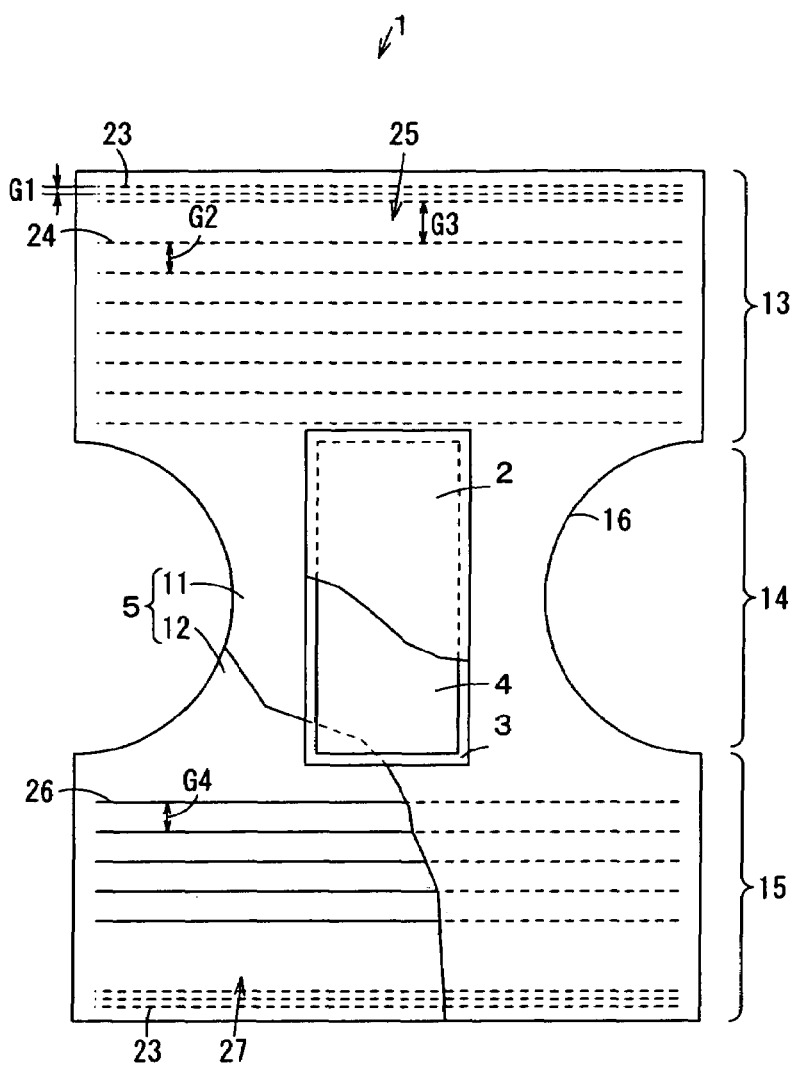
F I G. 1
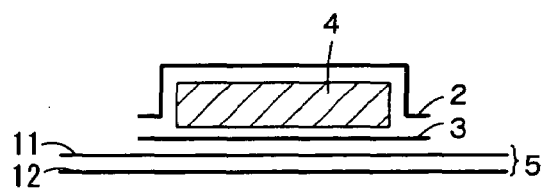
F I G. 2

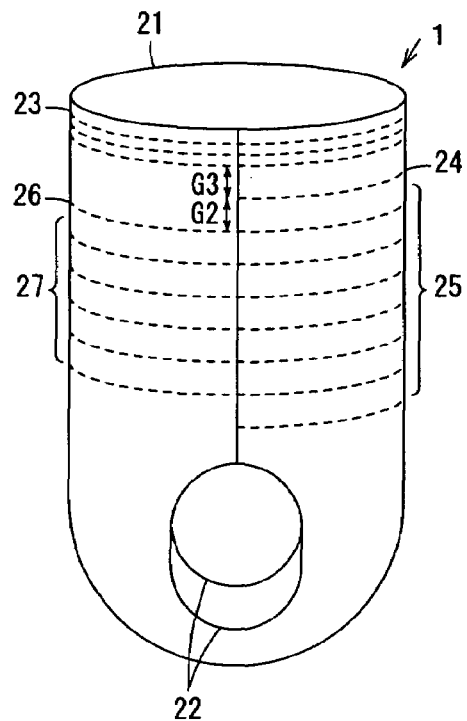
F I G. 5
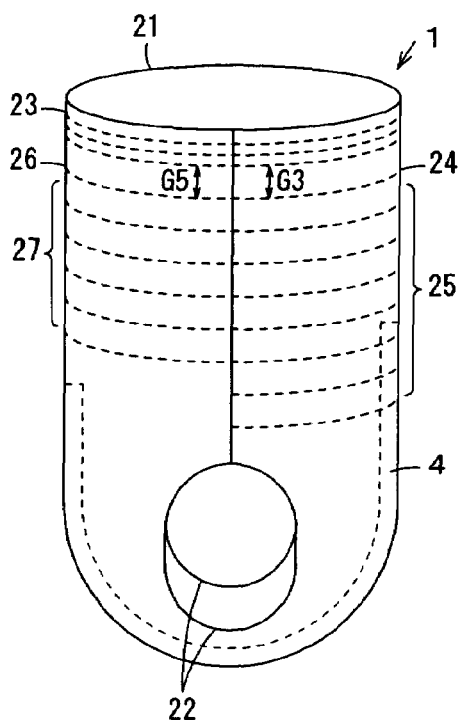
F I G. 6

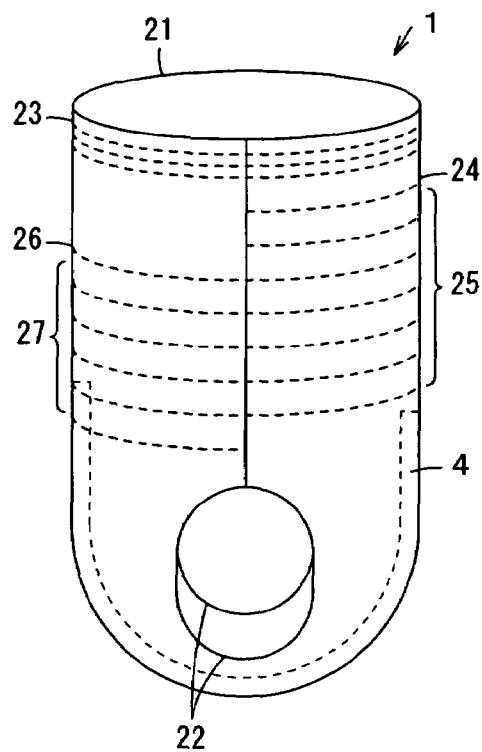
F I G. 7
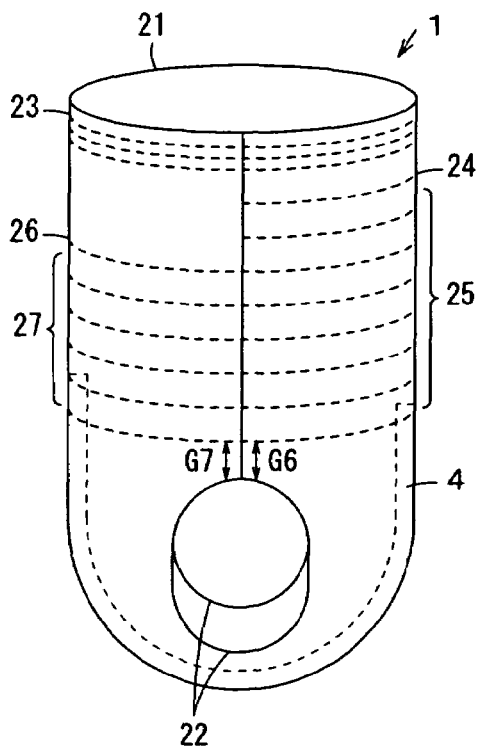
F I G. 8

DISPOSABLE ABSORBENT ARTICLE

TECHNICAL FIELD

The present invention relates to a disposable absorbent article that may be used, for example, by an adult as an incontinence product or other such purposes.

BACKGROUND OF THE INVENTION

A conventional disposable absorbent article of this type has an absorbent article body that typically comprises an absorbent pad and a cover sheet provided over the outer surface of the absorbent pad, i.e. the surface that faces the garment of the wearer. The absorbent pad comprises a liquid-permeable topsheet, a liquid-impermeable backsheet, and an absorbent core disposed therebetween. The absorbent article body has a rear waist region, a crotch region, and a front waist region, which are integrally arranged in the longitudinal direction from rear to front. The absorbent article body is pre-formed in a briefs-like shape by joining each side edge portion of the rear waist region and the corresponding side edge portion of the front waist region so as to form a waist opening and a pair of leg openings. Waist opening elastic members are provided circumferentially around the waist opening. The rear waist region and the front waist region are respectively provided with rear waist elastic members and front waist elastic members (an example is shown in Japanese Patent Laid-open No. 2002-165820).

However, a disposable absorbent article having the configuration described above is formed in such a briefs-like shape that the rear waist elastic members and the front waist elastic members are positioned almost exactly opposite each other in nearly the same number and provide approximately the same stretchability ratio. Therefore, should the tensile stress of the rear waist elastic members and the front waist elastic members be insufficient, there is the possibility of the briefs slipping down due to a poor body-hugging capability.

Consequently, in order to increase the body-hugging capability and prevent slippage and leakage, manufacturers of such articles generally provide the absorbent article body with a substantial tensile stress. This, however, may give the wearer an unnecessarily strong constricting feeling. Particularly when the wearer has a bulging lower abdomen, the wearer may feel it too tight at the lower abdomen.

Should the wearer tend to slouch due to advanced age or other reasons, the rear waist elastic members and the front waist elastic members having the same tensile stress may result in the absorbent article body slipping down from the buttock.

In order to solve the above problems, an object of the invention is to provide a disposable absorbent article that has superior body-hugging capability, is free from the problem of slippage, and has reduced constrictiveness.

DISCLOSURE OF THE INVENTION

A disposable absorbent article according to the present invention includes an absorbent article body comprising a liquid-permeable topsheet, a liquid-impermeable backsheet, an absorbent core disposed between the liquid-permeable topsheet and the liquid-impermeable backsheet, and a cover sheet attached to the outer surface of the liquid-impermeable backsheet. The aforementioned absorbent article body has a rear waist region, a crotch region, and a front waist region, which are integrally arranged in the longitudinal direction of the absorbent article body. The rear waist region and the front waist region are adapted to be respectively located at the rear and front waist side of the wearer. The crotch region has leg opening portions at both lateral side edges thereof. By joining each side edge portion of the rear waist region and the corresponding side edge portion of the front waist region, a waist opening becomes formed around the waist of the wearer and a pair of leg openings become formed around the upper thighs of the wearer. The absorbent article body also has one or more waist opening elastic members extending circumferentially around the waist opening, a plurality of rear waist elastic members that are stretchable in the widthwise direction of the absorbent article body, and a plurality of front waist elastic members that are stretchable in the widthwise direction of the absorbent article body. The aforementioned rear waist elastic members form a rear elastic area in the rear waist region. The aforementioned front waist elastic members form a front elastic area in the front waist region. A greater number of rear waist elastic members are provided than front waist elastic members. The rear elastic area is broader than the front elastic area with respect to the longitudinal direction of the absorbent article body. By providing the rear waist region and the front waist region respectively with rear waist elastic members and front waist elastic members, all of which are stretchable in the widthwise direction of the absorbent article body, so as to form a rear elastic area and a front elastic area, the rear waist region and the front waist region are enabled to stretch or contract in unison at the rear and front of the wearer, and the body-hugging capability of the disposable absorbent article around the waist is improved. Furthermore, by providing a greater number of rear waist elastic members than front waist elastic members and making the rear elastic area broader than the front elastic area with respect to the longitudinal direction of the absorbent article body, the body-hugging capability of the disposable absorbent article at the rear waist side of the wearer is increased so that the disposable absorbent article is prevented from slipping down, while constrictive feeling given by the disposable absorbent article is reduced so as not to be excessively tight at the front waist side of the wearer.

According to another feature of the invention, the rear waist elastic members of the disposable absorbent article are arrange so that the distance between each rear waist elastic member and its adjacent rear waist elastic member is nearly equal to the distance between each front waist elastic member and its adjacent front waist elastic member and that, when each side edge portion of the rear waist region and the corresponding side edge portion of the front waist region are joined, both ends of some number of rear waist elastic members are respectively connected to the ends of the corresponding front waist elastic members. By arranging the rear waist elastic members of the disposable absorbent article so that the distance between each rear waist elastic member and its adjacent rear waist elastic member is nearly equal to the distance between each front waist elastic member and its adjacent front waist elastic member and that, when each side edge portion of the rear waist region and the corresponding side edge portion of the front waist region are joined, both ends of some number of rear waist elastic members are respectively connected to the ends of the corresponding front waist elastic members, the rear waist region and the front waist region are enabled to be closely joined to each other around the entire waist of the wearer and thereby prevent the disposable absorbent article from slipping down.

According to yet another feature of the invention, the distance between the waist opening elastic members of the disposable absorbent article and the portion of the rear waist elastic members closest to the waist opening elastic members is nearly equal to the aforementioned distance between each rear waist elastic member and its adjacent rear waist elastic member. With the configuration as above, wherein the distance between the waist opening elastic members and the portion of the rear waist elastic members closest to the waist opening elastic members is nearly equal to the distance between each rear waist elastic member and its adjacent rear waist elastic member, the waist opening elastic members and the rear waist elastic members are arranged evenly in the rear waist side of the wearer. This configuration makes the entire rear waist region serves as an elastic area so that the entire rear waist region, which extends from the elastic area formed of the waist opening elastic members to the rear elastic area, be able to stretch in unison. Therefore, the disposable absorbent article is provided with a closer fit so as to be more reliably prevented from slipping down.

According to yet another feature of the invention, the distance between the waist opening elastic members of the disposable absorbent article and the portion of the rear waist elastic members closest to the waist opening elastic members is nearly equal to the distance between the waist opening elastic members and the portion of the front waist elastic members closest to the waist opening elastic members, and the absorbent core is arranged so as not to overlap the front elastic area while overlapping at least a part of the rear elastic area. As the distance between the waist opening elastic members and the portion of the rear waist elastic members closest to the waist opening elastic members is nearly equal to the distance between the waist opening elastic members and the portion of the front waist elastic members closest to the waist opening elastic members, all of the waist opening side of the rear waist region and the front waist region serve as an elastic area so that the rear waist region and the front waist region are closely joined to each other around the entire waist of the wearer and thereby prevent the disposable absorbent article from slipping down. Furthermore, as the absorbent core overlaps at least a part of the rear elastic area, the absorbent core closely fits at the rear waist side of the wearer and prevents leakage of urine or other discharged fluids without the absorbent core extending into the rear waist region any further than necessary.

According to yet another feature of the invention, the portion of the front waist elastic members of the disposable absorbent article closest to the leg opening portions is located closer to the leg opening portions than is the portion of the rear waist elastic members closest to the leg opening portions, and the absorbent core is arranged so as not to overlap the rear elastic area while overlapping at least a part of the front elastic area. As the portion of the front waist elastic members closest to the leg opening portions 16 is located closer to the leg opening portions than is the portion of the rear waist elastic members closest to the leg opening portions, the disposable absorbent article is prevented from being too tight at the front waist side of the wearer. Furthermore, as the absorbent core is provided so as to overlap at least a part of the front elastic area, the absorbent core closely fits at the front waist side of the wearer and prevents leakage without the absorbent core extending into the front waist region any further than necessary.

According to yet another feature of the invention, the distance between the leg opening portions of the disposable absorbent article and the portion of the rear waist elastic members closest to the leg opening portions is nearly equal to the distance between the leg opening portions and the portion of the front waist elastic members closest to the leg opening portions, and the absorbent core is arranged so as not to overlap the rear elastic area while overlapping at least a part of the front elastic area. As the distance between the leg opening portions and the portion of the rear waist elastic members closest to the leg opening portions is nearly equal to the distance between the leg opening portions and the portion of the front waist elastic members closest to the leg opening portions, all of the waist opening side of the rear waist region and the front waist region serve as an elastic area so that the rear waist region and the front waist region are closely joined to each other around the entire waist of the wearer. Furthermore, as the absorbent core overlaps at least a part of the front elastic area, the absorbent core closely fits at the front waist side of the wearer and prevents leakage without the absorbent core extending into the front waist region any further than necessary.

BRIEF DESCRIPTION OF THE DRAWINGS

FIG. 1 is a top view of a practical example of a disposable absorbent article according to a first embodiment of the present invention;

FIG. 2 is a vertical sectional view of the aforementioned disposable absorbent article;

FIG. 5 is a perspective of yet another working example of the disposable absorbent article;

FIG. 6 is a perspective of a disposable absorbent article according to a second embodiment of the present invention;

FIG. 7 is a perspective of a disposable absorbent article according to a third embodiment of the present invention; and FIG. 8 is a perspective of another working example of the disposable absorbent article according to the third embodiment of the present invention.

PREFERRED EMBODIMENT OF THE INVENTION

Figure 3:
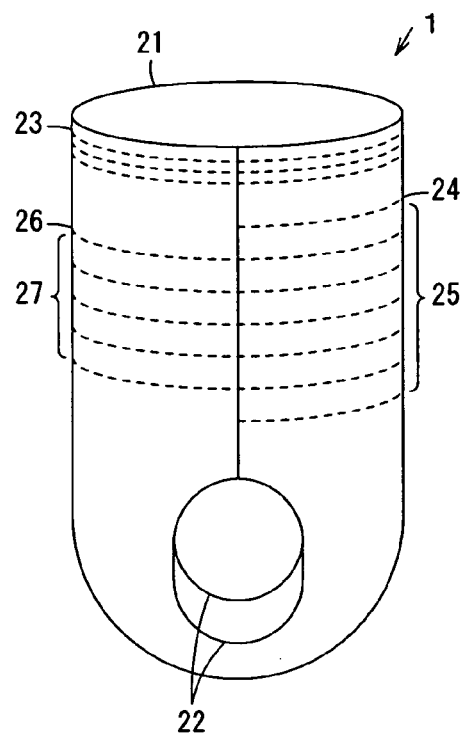
FIG. 3 is a perspective of the disposable absorbent article.

Next, the configuration of a disposable absorbent article according to the first embodiment of the present invention is explained hereunder, referring to FIGS. 1 through 3.

The disposable absorbent article shown in FIG. 1 is, for example, a disposable paper diaper and has a diaper body 1 serving as an absorbent article body. The diaper body 1 is formed from the flat-out state shown in FIG. 1 into a briefs-like shape shown in FIG. 3 so that the wearer, who may have health problems or suffer from incontinence, can put it around the portion of the body from the rear waist to the front waist. The diaper body 1 has a layered structure consisting of a liquid-permeable topsheet 2 that can pass liquid, a liquid-impermeable backsheet 3 that does not allow liquids to pass, an absorbent core 4 that is disposed between the liquid-permeable topsheet 2 and the liquid-impermeable backsheet 3 and capable of absorbing liquids, and a cover sheet 5 bonded to the outer surface of the liquid-impermeable backsheet 3.

The liquid-permeable topsheet 2 and the liquid-impermeable backsheet 3 are bonded to each other along the outer edges with a bonding agent or any other appropriate means, with the absorbent core 4 sealed between the two sheets.

The liquid-permeable topsheet 2 is made of a sheet material such as a woven fabric, nonwoven fabric, porous film, or synthetic resin. To be more specific, the liquid-permeable topsheet 2 is made of a sheet material that is liquid permeable as well as gas permeable and has a similar texture to underwear so that the liquid-permeable topsheet 2 facilitates passage of discharged fluids, such as urine, to the absorbent core 4 while avoiding discomfort for the wearer in spite of being worn next to the skin.

The liquid-impermeable backsheet 3 is made of a sheet material, such as polyethylene or any other appropriate synthetic resin, that is gas permeable but impermeable to liquid so as to prevent urine or other discharged fluids from soiling clothes, such as underwear, or bed sheets.

The absorbent core 4 is formed in a sheet-like shape of a material that contains pulp or a similar material as the principal component, as well as such other materials as a super absorbent polymer so that the absorbent core 4 has sufficient capability to absorb urine or other discharged fluids.

As shown in FIG. 1, the liquid-permeable topsheet 2, the liquid-impermeable backsheet 3, and the absorbent core 4 all have a rectangular shape and are placed at the approximate center of the cover sheet 5 so that the long sides of the rectangular shape extend in the longitudinal direction of the diaper body 1.

As shown in FIGS. 1 and 2, the cover sheet 5 is larger than the liquid-permeable topsheet 2, the liquid-impermeable backsheet 3, or the absorbent core 4. The cover sheet 5 is formed of an inner sheet 11 and an outer sheet 12, which are layered one on top of the other and integrally bonded to each other. Both the inner sheet 11 and the outer sheet 12 are gas permeable but impermeable to liquid. The outer surface of the liquid-impermeable backsheet 3 is bonded to the inner sheet 11 with a bonding agent or any other appropriate means.

The cover sheet 5 consists of a rear waist region 13, a crotch region 14, and a front waist region 15, which are integrally arranged, when viewed in the flat-out state, in the longitudinal direction of the diaper body 1. When in use, the rear waist region 13 and the front waist region 15 are respectively located at the rear and front waist side of the wearer. As a whole, the cover sheet 5 has a generally rectangular shape that is symmetrical with respect to the center line that extends in the longitudinal direction. Each lateral side edge portion of the crotch region 14 is cut out in an arc so as to form a leg opening portion 16.

The liquid-permeable topsheet 2, the liquid-impermeable backsheet 3, and the absorbent core 4 are positioned so as to extend in the longitudinal direction of the cover sheet 5 of the diaper body 1 so that the longitudinal center line of the liquid-permeable topsheet 2, the liquid-impermeable backsheet 3, and the absorbent core 4 essentially corresponds to the longitudinal center lines of the rear waist region 13, the crotch region 14, and the front waist region 15.

The rear waist region 13 of the cover sheet 5 of the diaper body 1 is located at one of the longitudinal ends of the diaper body 1 as viewed in the flat-out state. When the diaper body 1 is folded to an appropriate degree from the flat-out state, the rear waist region 13 becomes the portion that will be located at the buttock of the wearer. A rear waist bonding portion (not shown) is formed along each side edge of the rear waist region 13.

The crotch region 14 of the diaper body 1 is located at the longitudinal middle of the diaper body 1 as viewed in the flat-out state, located between the rear waist region 13 and the front waist region 15 as an integral, continuous body therewith. When the diaper body 1 is folded to an appropriate degree from the flat-out state, the crotch region 14 becomes the portion that will be located at the crotch of the wearer.

The front waist region 15 of the diaper body 1 is located at the other longitudinal end of the diaper body 1 as viewed in the flat-out state, i.e. the opposite end of the rear waist region 13, as an integral, continuous body with the crotch region 14. When the diaper body 1 is folded to an appropriate degree from the flat-out state, the front waist region 15 becomes the portion that will be located at the abdomen of the wearer. The front waist region 15 has an approximately rectangular shape longer in the lateral direction of the diaper body 1 than the longitudinal direction, the same configuration as the rear waist region 13.

A front waist bonding portion (not shown) for attachment to the corresponding rear waist bonding portion of the rear waist region 13 is formed near each side edge of the front waist region 15. By attaching each front waist bonding portion to the corresponding rear waist bonding portion, a waist opening 21 is defined by the rear waist region 13 and the front waist region 15 around the waist of the wearer while a pair of leg openings 22 are defined by the two leg opening portions 16. Thus, as shown in FIG. 3, the diaper body 1 is formed into a briefs-like shape.

As shown in FIG. 1, between the inner sheet 11 and the outer sheet 12, the rear waist region 13 and the front waist region 15 are respectively provided with a plurality of waist opening elastic members 23 (for example three elastic members). The waist opening elastic members 23 are made of an elastic material, such as elastic threads, and affixed to the rear waist region 13 and the front waist region 15 with a bonding agent or any other appropriate means, in such a state as to be stretched laterally across the rear waist region 13 and the front waist region 15. The waist opening elastic members 23 are arranged at equal intervals G1 (G1 may desirably range between 2 mm and 7 mm) in the longitudinal direction of the diaper body 1. In other words, when the diaper body 1 is in the briefs-like shape shown in FIG. 3, the waist opening elastic members 23 extend circumferentially around the waist opening 21. The waist opening elastic members 23 thus provided give elasticity to nearly the entire area of the rear waist region and the front waist region, in other words nearly the entire waist of the wearer.

A plurality of rear waist elastic members 24 are provided between the inner sheet 11 and the outer sheet 12 of the rear waist region 13. The rear waist elastic members 24 are made of an elastic material, such as elastic threads, and affixed to the rear waist region 13 with a bonding agent or any other appropriate means, in such a state as to be stretched laterally across the rear waist region 13. The rear waist elastic members 24 are arranged at equal intervals (desirably 2 to 6 members per 5 cm) in the longitudinal direction of the diaper body 1. In the case of the present embodiment, the rear waist elastic members 24 consist of seven elastic members that are arranged at intervals G2, wherein G2 ranges from 8 mm to 20 mm. Therefore, the rear waist elastic members 24 are arranged at wider intervals than are the waist opening elastic members 23. In other words, the waist opening elastic members 23 are spaced more closely to one another than are the rear waist elastic members 24 and can be expressed as G1<G2.

As the rear waist elastic members 24 are stretchable laterally across the rear waist region 13, the rear waist region 13 can be stretched in widthwise direction of the diaper body 1 by stretching the rear waist elastic members 24. As shown in FIG. 3, a rear elastic area 25 is formed in the rear waist region 13 by the rear waist elastic members 24.

It is desirable that the tensile stress of the rear elastic area 25 range from 1.5 to 2.0 N. In order to achieve such a stress, each rear waist elastic member 24 may desirably be stretched with a tensile stress of 0.08 to 2.5 N and a 1.5-to 3.0-fold stretching ratio.

The distance G3 between the waist opening elastic members 23 and the portion of the rear waist elastic members 24 that is closest to the waist opening elastic members 23, in other words the uppermost rear waist elastic member 24 as viewed in FIG. 3, is greater than the distance G2 between each rear waist elastic member 24 and its adjacent rear waist elastic member 24 (G2<G3).

A plurality of front waist elastic members 26 are provided between the inner sheet 11 and the outer sheet 12 of the front waist region 15.

The front waist elastic members 26 are made of an elastic material, such as elastic threads, and affixed to the front waist region 15 with a bonding agent or any other appropriate means, in such a state as to be stretched laterally across the front waist region 15. The front waist elastic members 26 are arranged at equal intervals (desirably 2 to 6 members per 5 cm) in the longitudinal direction of the diaper body 1. In the case of the present embodiment, the front waist elastic members 26 consist of five elastic members that are arranged at intervals G4, wherein G2 ranges from 8 mm to 20 mm. Therefore, there are fewer front waist elastic members 26 than rear waist elastic members 24, and the front waist elastic members 26 are arranged at wider intervals than are the waist opening elastic members 23. In other words, a greater number of rear waist elastic members 24 are provided than front waist elastic members 26, and the waist opening elastic members 23 are spaced more closely to one another than are the front waist elastic members 26.

As the front waist elastic members 26 are stretchable laterally across the front waist region 15, the front waist region 15 can be stretched in widthwise direction of the diaper body 1 by stretching the front waist elastic members 26. A front elastic area 27 is formed in the front waist region 15 by the front waist elastic members 26.

It is desirable that the tensile stress of the front elastic area 27 range from 1.0 to 1.5 N. In order to achieve such a stress, each front waist elastic member 26 may desirably be stretched with a tensile stress of 0.08 to 2.5 N and a 1.5-to 3.0-fold stretching ratio.

The front waist elastic members 26 are arranged so that the portion closest to the waist opening elastic members 23, i.e. the front waist elastic member 26 that is closest to the waist opening 21, correspond to the portion of the rear waist elastic members 24 second-closest to the waist opening elastic members 23, in other words the second-from-the-top rear waist elastic member 24 as viewed in FIG. 3, when the diaper body 1 is formed into the briefs-like shape. Therefore, when the diaper body 1 is formed into the briefs-like shape, the two lateral ends of the front waist elastic member 26 closest to the waist opening 21 are connected to the respective lateral ends of the second-from-the-top rear waist elastic member 24 as viewed in FIG. 3.

The distance G4 between each front waist elastic member 26 and its adjacent front waist elastic member 26 is nearly equal to the distance G2 between each rear waist elastic member 24 and its adjacent rear waist elastic member 24 (G2≈G4). Therefore, the front elastic area 27 is shorter in the longitudinal direction of the diaper body 1 than the rear elastic area 25. In other words, the rear elastic area 25 is broader than the front elastic area 27 with respect to the longitudinal direction of the diaper body 1. As a result, when the diaper body 1 is formed into the briefs-like shape as shown in FIG. 3, the ends of the front waist elastic members 26 are respectively connected to the ends of the second-through-fifth-from-the-top rear waist elastic members 24 as viewed in FIG. 3.

The stretchability of the front waist elastic members 26 should desirably be adjusted so that the stretchability ratio of the front elastic area 27 does not exceed that of the rear elastic area 25. This can be achieved by, for example, using a different material from that of the rear waist elastic members 24 or the same material with different characteristics, such as thickness.

Leg opening elastic members (not shown) made of elastic threads or other appropriate material are provided, in a stretched state, between the inner sheet 11 and the outer sheet 12 of the cover sheet 5, near each leg opening portion 16. As a result of the provision of the leg opening elastic members, each leg opening portion 16 is shirred so as to be elastic both in the longitudinal direction and the widthwise direction of the diaper body 1.

Next, the function and effects of the first embodiment described above are explained hereunder.

To use, the diaper body 1 is formed into a briefs-like shape shown in FIG. 3 so that it can be worn like underpants.

By providing a plurality of rear waist elastic members 24 so as to be stretchable in the widthwise direction of the diaper body 1, a rear elastic area 25 is formed in the rear waist region 13. By providing a plurality of front waist elastic members 26 so as to be stretchable in the widthwise direction of the diaper body 1, a front elastic area 27 is formed in the front waist region 15. Therefore, the rear waist region 13 and the front waist region 15 are capable of stretching or contracting in unison at the rear and front of the wearer so that the body-hugging capability of the diaper body 1 around the waist is improved.

By providing a greater number of rear waist elastic members 24 than the front waist elastic members 26 and forming the rear elastic area 25 so as to be broader than the front elastic area 27 with respect to the longitudinal direction of the diaper body 1, the diaper body 1 is provided with a closer fit at the rear waist side of the wearer and thereby prevented from slipping down. This is especially effective for a wearer of advanced age who tends to slouch. While having these effects, the configuration described above reduces constrictive feeling given to the wearer by ensuring that the diaper body 1 is not excessively tight at the front waist side of the wearer.

The distance G2 between each rear waist elastic member 24 and its adjacent rear waist elastic member 24 is nearly equal to the distance G4 between each front waist elastic member 26 and its adjacent front waist elastic member 26. Furthermore, when each side edge portion of the rear waist region 13 is joined to the corresponding side edge portion of the front waist region 15, the ends of the second-through-fifth-from-the-top rear waist elastic members 24 as viewed in FIG. 3 are respectively connected to the ends of the front waist elastic members 26. This configuration ensures that the rear waist region 13 and the front waist region 15 are closely joined to each other around the entire waist of the wearer and thereby prevents the diaper body 1 from slipping down.

The waist opening elastic members 23 are arranged so that the distance G1 between each waist opening elastic member 23 and its adjacent waist opening elastic member 23 are shorter than the distance G4 between each front waist elastic member 26 and its adjacent front waist elastic member 26. Thus arranging the waist opening elastic members 23 increases the body-hugging capability of the diaper body 1 around the waist of the wearer, thereby increasing reliability and more reliably preventing the diaper body 1 from slipping down, holds down production costs by keeping the numbers of elastic members required for the rear waist region 13 and the front waist region 15 to a minimum, and also limits the tensile stress of the rear waist region 13 and the front waist region 15 to an appropriate, sufficient degree so as not to apply excessive constriction to the wearer.

An insufficient tensile stress, i.e. less than 1.0 N, of the rear elastic area 25 or the front elastic area 27 may cause the diaper body 1 to slip down the wearer's body after the wearer urinates, while a tensile stress greater than 2.0 N presents the possibility of excessive constriction, resulting in the rear waist elastic members 24 or the front waist elastic members 26 leaving impressions, in other words stretch marks, on the wearer's skin. In the case of the present embodiment, however, the tensile stress of the rear elastic area 25 and the tensile stress of the front elastic area 27 are respectively limited within the ranges of 1.5 to 2.0 N and 1.0 to 1.5 N. Therefore, the constrictive feeling is reduced, and the diaper body 1 is prevented from slippage, even after the wearer urinates.

Furthermore, making the tensile stress of the rear elastic area 25 greater than the tensile stress of the front elastic area 27 provides the diaper body 1 with a closer fit at the rear waist side.

Figure 4:
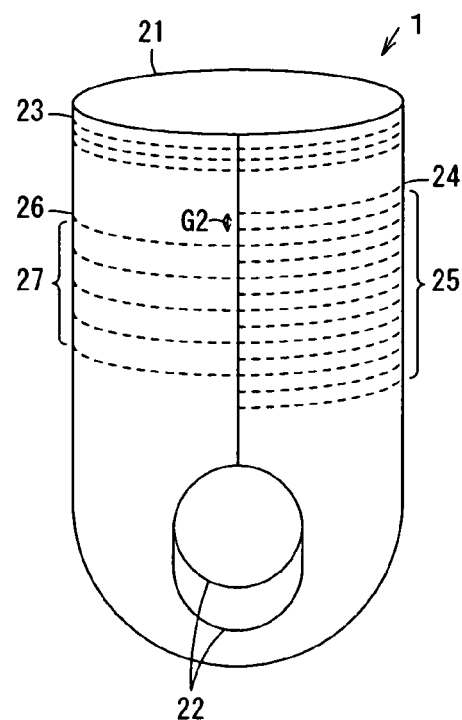
FIG. 4 is a perspective of another practical example of the same.

As shown in FIG. 4, the diaper body 1 according to the first embodiment described above may be provided with a greater number of rear waist elastic members 24 than in the case of the configuration shown in FIGS. 1 to 3, with the distance G2 between each rear waist elastic member 24 and its adjacent rear waist elastic member 24 reduced. In the case of the example shown in FIG. 4, thirteen rear waist elastic members 24 are provided, with the distance G2 between each rear waist elastic member 24 and its adjacent rear waist elastic member 24 reduced to approximately half of the distance G2 in the configuration shown in FIGS. 1 to 3. As this configuration further increases the stretchability of the rear waist region 13 and thereby provides the rear waist region 13 with a closer fit at the rear waist side of the wearer, it prevents slippage of the diaper body 1 more reliably.

Yet another configuration example is shown in FIG. 5, wherein the distance G3 between the waist opening elastic members 23 and the rear waist elastic members 24 is nearly equal to the distance G2 between each rear waist elastic member 24 and its adjacent rear waist elastic member 24. This configuration makes the entire rear waist region 13 elastic so that the entire rear waist region 13, which extends from the elastic area formed of the waist opening elastic members 23 to the rear elastic area 25, is able to stretch in unison. Therefore, the diaper body 1 is provided with a closer fit at the rear waist side and is therefore more reliably prevented from slipping down.

In yet another alternative configuration, the lateral ends of the rear waist elastic members 24 are positioned alternately with the corresponding ends of the front waist elastic members 26 instead of forming a continuous line when the diaper body 1 is formed into the briefs-like shape shown in FIG. 3.

Neither the rear waist elastic members 24 nor the front waist elastic members 26 are limited to a particular material; for example, each rear waist elastic member 24 may have a smaller stretchability ratio than that of each front waist elastic member 26, provided that the stretchability ratio of the rear elastic area 25 is greater than that of the front elastic area 27. This can be achieved by further increasing the number of the rear waist elastic members 24 or other appropriate means.

Next, the second embodiment of the present invention is explained, referring to FIG. 6.

The embodiment shown in FIG. 6 has a configuration basically similar to that of the embodiment shown in FIGS. 1 to 3 described above. However, a diaper body 1 according to this embodiment is provided with a plurality of rear waist elastic members 24, for example eight rear waist elastic members, between the inner sheet 11 and the outer sheet 12 of the rear waist region 13.

Furthermore, a plurality of front waist elastic members 26, for example six front waist elastic members, are provided between the inner sheet 11 and the outer sheet 12 of the front waist region 15.

The distance G3 between the waist opening elastic members 23 and the portion of the rear waist elastic members 24 that is closest to the waist opening elastic members 23, in other words the uppermost rear waist elastic member 24 as viewed in FIG. 6, is nearly equal to the distance G5 between the waist opening elastic members 23 and the portion of the front waist elastic members 26 that is closest to the waist opening elastic members 23, in other words the uppermost front waist elastic member 26 as viewed in FIG. 6.

As a result, when the diaper body 1 is formed into a briefs-like shape as shown in FIG. 6, the ends of the front waist elastic members 26 are respectively connected to the ends of the six uppermost rear waist elastic members 24 as viewed in FIG. 6.

The absorbent core 4 is arranged so as not to overlap the front elastic area 27 while overlapping the portion of the rear elastic area 25 near the leg opening portions 16, for example the three bottommost rear waist elastic members 24 as viewed in FIG. 6.

To use, the diaper body 1 is formed into a briefs-like shape shown in FIG. 6 so that it can be worn like underpants. In this state, all of the waist opening 21 side of the rear waist region 13 and the front waist region 15 serve as an elastic area. This configuration ensures that the rear waist region 13 and the front waist region 15 are closely joined to each other around the entire waist of the wearer and thereby prevents the diaper body 1 from slipping down.

The absorbent core 4 is provided so as to partially overlap the rear elastic area 25. Therefore, even if the absorbent core 4 is positioned so as to extend into the rear waist region 13 and the front waist region 15 to the same extent, the absorbent core 4 closely fits at the rear waist side of the wearer. In other words, the embodiment shown in FIG. 6 prevents leakage of urine or other discharged fluids without the absorbent core 4 extending into the rear waist region 13 any further than necessary.

Next, the third embodiment of the present invention is explained, referring to FIG. 7.

The embodiment shown in FIG. 7 has a configuration basically similar to that of the embodiment shown in FIGS. 1 to 3 described above. However, a diaper body 1 according to this embodiment is provided with a plurality of rear waist elastic members 24, for example seven rear waist elastic members, between the inner sheet 11 and the outer sheet 12 of the rear waist region 13.

Furthermore, a plurality of front waist elastic members 26, for example six front waist elastic members, are provided between the inner sheet 11 and the outer sheet 12 of the front waist region 15.

The front waist elastic members 26 are arranged so that the portion that is closest to the leg opening portions 16 is located closer to the leg opening portions 16 than is the portion of the rear waist elastic members 24 that is closest to the leg opening portions 16. In other words, the bottommost front waist elastic member 26 as viewed in FIG. 7 is located lower than the bottommost rear waist elastic member 24 as viewed in FIG. 7.

Furthermore, the portion that is closest to the waist opening elastic members 23, i.e. the uppermost front waist elastic member 26 as viewed in FIG. 7, corresponds to the third-from-the-top rear waist elastic member 24 as viewed in FIG. 7, when the diaper body 1 is formed into the briefs-like shape shown in FIG. 7.

Therefore, when the diaper body 1 is formed into a briefs-like shape as shown in FIG. 7, the lateral ends of the five uppermost front waist elastic members 26 as viewed in FIG. 7 are respectively connected to the ends of the third-through-seventh-from-the-top rear waist elastic members 24 as viewed in FIG. 7.

The absorbent core 4 is arranged so as not to overlap the rear elastic area 25 while overlapping the portion of the front elastic area 27 near the leg opening portions 16, for example the two bottommost front waist elastic members 26 as viewed in FIG. 7.

To use, the diaper body 1 is formed into a briefs-like shape shown in FIG. 7 so that it can be worn like underpants.

As the portion that is closest to the leg opening portions 16 is located closer to the leg opening portions 16 than is the portion of the rear waist elastic members 24 that is closest to the leg opening portions 16, the diaper body 1 is prevented from being too tight at the front waist side of the wearer.

The absorbent core 4 is provided so as to partially overlap the front elastic area 27. Therefore, even if the absorbent core 4 is positioned so as to extend into the rear waist region 13 and the front waist region 15 to the same extent, the absorbent core 4 closely fits at the front waist side of the wearer. In other words, the embodiment shown in FIG. 7 prevents leakage without the absorbent core 4 extending into the front waist region 15 any further than necessary.

As shown in FIG. 8, the rear waist elastic members 24 and the front waist elastic members 26 of the diaper body 1 according to the third embodiment described above may be arranged so that the distance G6 between the leg opening portions 16 and the portion of the rear waist elastic members 24 that is closest to the leg opening portions 16, i.e. the bottommost rear waist elastic member 24 as viewed in FIG. 8, is nearly equal to the distance G7 between the leg opening portions 16 and the portion of the front waist elastic members 26 that is closest to the leg opening portions 16, i.e. the bottommost front waist elastic member 26 as viewed in FIG. 8. Therefore, all of the leg opening portions 16 side of the rear waist region 13 and the front waist region 15 serve as an elastic area so that the rear waist region 13 and the front waist region 15 are closely joined to each other around the entire waist of the wearer.

In any one of the embodiments described above, the tensile stress and the stretching ratio of each rear waist elastic member 24 and/or front waist elastic member 26 may be arbitrarily changed in accordance with the number or any other characteristics of the rear waist elastic members 24 or the front waist elastic members 26, provided that the rear elastic area 25 and the front elastic area 27 respectively have the desired tensile stresses.

POSSIBLE INDUSTRIAL APPLICATION

As described above, a disposable absorbent article according to the invention may be used, for example, as a disposable diaper, an incontinence product or other such purposes for an adult.

The invention claimed is:

1. A disposable absorbent article including an absorbent article body which comprises a liquid-permeable topsheet, a liquid-impermeable backsheet, an absorbent core disposed between said liquid-permeable topsheet and said liquid-impermeable backsheet, and a cover sheet attached to the outer surface of said liquid-impermeable backsheet, wherein;

said absorbent article body has a rear waist region, a crotch region, and a front waist region, which are integrally arranged in the longitudinal direction of said absorbent article body, said rear waist region and said front waist region adapted to be respectively located at the rear and front waist side of a wearer, and said crotch region has leg opening portions at both lateral side edges thereof;

by joining each side edge portion of said rear waist region and the corresponding side edge portion of said front waist region, a waist opening becomes formed around the waist of the wearer and a pair of leg openings become formed around the upper thighs of the wearer;

said absorbent article body also has;

one or more waist opening elastic members extending circumferentially around said waist opening, a plurality of rear waist elastic members that are stretchable in the widthwise direction of said absorbent article body, and a plurality of front waist elastic members that are stretchable in the widthwise direction of said absorbent article body;

said rear waist elastic members form a rear elastic area in said rear waist region;

said front waist elastic members form a front elastic area in said front waist region;

a greater number of rear waist elastic members are provided than front waist elastic members; and said rear elastic area is broader than said front elastic area with respect to the longitudinal direction of said absorbent article body;

said rear waist elastic members are arranged so that the distance between each rear waist elastic member and its adjacent rear waist elastic member is approximately equal to the distance between each front waist elastic member and its adjacent front waist elastic member and that, when each side edge portion of said rear waist region and the corresponding side edge portion of said front waist region are joined, both ends of some but less than all of said rear waist elastic members are respectively connected to the ends of the corresponding front waist elastic members;

said distance between said waist opening elastic members and the portion of said rear waist elastic members closest to said waist opening elastic members is approximately equal to the distance between said waist opening elastic members and the portion of said front waist elastic members closest to said waist opening elastic members, and said absorbent core is ranged so as not to overlap said front elastic area while overlapping at least a part of said rear elastic area.

2. The disposable absorbent article according to claim 1, wherein:

the distance between said waist opening elastic members and the portion of said rear waist elastic members closest to said waist opening elastic members is approximately equal to said distance between each rear waist elastic member and its adjacent rear waist elastic member.

3. A disposable absorbent article including an absorbent article body which comprises a liquid-permeable topsheet, a liquid-impermeable backsheet, an absorbent core disposed between said liquid-permeable topsheet and said liquid-impermeable backsheet, and a cover sheet attached to the outer surface of said liquid-impermeable backsheet, wherein:

said absorbent article body has a rear waist region, a crotch region, and a front waist region, which are integrally arranged in the longitudinal direction of said absorbent article body, said rear waist region and said front waist region adapted to be respectively located at the rear and front waist side of a wearer, and said crotch region has leg opening portions at both lateral side edges thereof;

by joining each side edge portion of said rear waist region and the corresponding side edge portion of said front waist region, a waist opening becomes formed around the waist of the wearer and a pair of leg openings become formed around the upper thighs of the wearer;

said absorbent article body also has;
  one or more waist opening elastic members extending circumferentially around said waist opening,
  a plurality of rear waist elastic members that are stretchable in the widthwise direction of said absorbent article body, and
  a plurality of front waist elastic members that are stretchable in the widthwise direction of said absorbent article body;
  said rear waist elastic members form a rear elastic area in said rear waist region;
  said front waist elastic members form a front elastic area in said front waist region;
  a greater number of rear waist elastic members are provided than front waist elastic members; and
  said rear elastic area is broader than said front elastic area with respect to the longitudinal direction of said absorbent article body;
  said rear waist elastic members are arranged so that the distance between each rear waist elastic member and its adjacent rear waist elastic member is approximately equal to the distance between each front waist elastic member and its adjacent front waist elastic member and that, when each side edge portion of said rear waist region and the corresponding side edge portion of said front waist region are joined, both ends of some but less than all of said rear waist elastic members are respectively connected to the ends of the corresponding front waist elastic members;
  the portion of said front waist elastic members closest to said leg opening portions is located closer to said leg opening portions than is the portion of said rear waist elastic members closest to said leg opening portions, and
  said absorbent core is arranged so as not to overlap said rear elastic area while overlapping at least a part of said front elastic area.

4. The disposable absorbent article according to claim 3, wherein:

the distance between said waist opening elastic members and the portion of said rear waist elastic members closest to said waist opening elastic members is approximately equal to said distance between each rear waist elastic member and its adjacent rear waist elastic member.

5. A disposable absorbent article including an absorbent article body which comprises a liquid-permeable topsheet, a liquid-impermeable backsheet, an absorbent core disposed between said liquid-permeable topsheet and said liquid-impermeable backsheet, and a cover sheet attached to the outer surface of said liquid-impermeable backsheet, wherein;

said absorbent article body has a rear waist region, a crotch region, and a front waist region, which are integrally arranged in the longitudinal direction of said absorbent article body, said rear waist region and said front waist region adapted to be respectively located at the rear and front waist side of a wearer, and said crotch region has leg opening portions at both lateral side edges thereof;

by joining each side edge portion of said rear waist region and the corresponding side edge portion of said front waist region, a waist opening becomes formed around the waist of the wearer and a pair of leg openings become formed around the upper thighs of the wearer;

said absorbent article body also has:
  one or more waist opening elastic members extending circumferentially around said waist opening,
  a plurality of rear waist elastic members that are stretchable in the widthwise direction of said absorbent article body, and
  a plurality of front waist elastic members that are stretchable in the widthwise direction of said absorbent article body;
  said rear waist elastic members form a rear elastic area in said rear waist region;
  said front waist elastic members form a front elastic area in said front waist region;
  a greater number of rear waist elastic members are provided than front waist elastic members; and
  said rear elastic area is broader than said front elastic area with respect to the longitudinal direction of said absorbent article body;
  said rear waist elastic members are arranged so that the distance between each rear waist elastic member and its adjacent rear waist elastic member is approximately equal to the distance between each front waist elastic member and its adjacent front waist elastic member and that, when each side edge portion of said rear waist region and the corresponding side edge portion of said front waist region are joined, both ends of some but less than all of said rear waist elastic members are respectively connected to the ends of the corresponding front waist elastic members;
  the distance separation between said leg opening portions and the portion of said rear waist elastic members closest to said leg opening portions is approximately equal to the distance between said leg opening portions and the portion of said front waist elastic members closest to said leg opening portions, and
  said absorbent core is arranged so as not to overlap said rear elastic area while overlapping at least a part of said front elastic area.

6. The disposable absorbent article according to claim 5, wherein:

the distance between said waist opening elastic members and the portion of said rear waist elastic members closest to said waist opening elastic members is approximately equal to said distance between each rear waist elastic member and its adjacent rear waist elastic member.

* * * * *